United States Patent [19]
Jonsson et al.

[11] Patent Number: 5,633,389
[45] Date of Patent: May 27, 1997

[54] THERMOREVERSIBLE COATING AND A PROCESS FOR ITS MANUFACTURE

[75] Inventors: Erik H. Jonsson, Coraopolis; Philip E. Yeske, Pittsburgh; Douglas A. Wicks, Mt. Lebanon, all of Pa.; Harald Pielartzik, Krefeld, Germany

[73] Assignee: Bayer Corporation, Pittsburgh, Pa.

[21] Appl. No.: 448,847

[22] Filed: May 24, 1995

[51] Int. Cl.$^6$ .................. C07D 233/78; C07D 233/72; C08G 18/46; C09D 175/02
[52] U.S. Cl. .................. 548/318.5; 528/49; 528/68; 528/69; 528/73; 528/75; 528/84; 548/300.1; 548/312.1; 548/313.7; 548/314.1; 548/314.4; 548/316.4; 548/317.1; 548/319.5
[58] Field of Search .................. 528/49, 69, 75, 528/68, 84, 73; 548/300.1, 312.1, 313.7, 314.1, 314.4, 316.4, 317.1, 318.5, 319.5

[56] References Cited

U.S. PATENT DOCUMENTS

| | | | |
|---|---|---|---|
| 3,549,599 | 12/1970 | Merten | 528/73 |
| 5,126,170 | 6/1992 | Zwiener et al. | 528/68 |
| 5,236,741 | 8/1993 | Zwiener et al. | 525/131 |
| 5,243,012 | 9/1993 | Wicks et al. | 528/58 |
| 5,412,056 | 5/1995 | Zwiener et al. | 528/73 |

FOREIGN PATENT DOCUMENTS 0133519  2/1985  European Pat. Off.

OTHER PUBLICATIONS

Kirk–Othmer, Encyclopedia of Chemical Technology, Third Edition vol. 12, John Wiley & Sons p. 692 et seq. 1980.

Chemical Reviews, Ralph Shriner Editor, vol. 46, 1950, pp. 406–470.

Rodd's Chemistry of Carbona Compounds, second ed. Edited by S. Coffey et al vol. IV, Part C Heterocyclic Compounds, Martin R. Ansell, Editor Elsevier, 1986, p. 185 et seq.

$\alpha,\beta$–Unsaturated Polyesters and Monomeric Maleic and FumaricEsters, Sung Ki Lee in Am. Chem. Soc. Div. of Organic Coatings & Plastic Chemistry, Miami Beach, Apr. 1967, 27(1).

*Primary Examiner*—Rabon Sergent
*Attorney, Agent, or Firm*—Joseph C. Gil; Aron Preis

[57] ABSTRACT

The invention relates to a thermoreversible process for the preparation of a hydantoin comprisng (a) reacting an unsaturated polyester with a monofunctional amine to yield a poly(ester aspartate), and (b) reacting said poly(ester aspartate) with an isocyanate to produce a poly(ester urea), and (c) heating said poly(ester urea) to form a hydantoin compound.

The process is useful for the preparation of coatings.

10 Claims, No Drawings

THERMOREVERSIBLE COATING AND A PROCESS FOR ITS MANUFACTURE

The invention relates to a thermoreversible coating based on poly(ester urea) and to a process for its manufacture.

Low molecular weight hydantoins are well known compounds and their uses as intermediates and ingredients in the chemical, pharmaceutical and consumer product industries are well documented—see for instance Kirk-Othmer, Encyclopedia of Chemical Technology, Third Edition Vol. 12, John Wiley & Sons pp. 692 et seq. Several synthesis routes of such compounds have been reported: see for instance page 701 of the cited encyclopedia where the preparation of hydantoin from amino acid and organic isocyanates is disclosed. Also relevant in this connection is the disclosure in Chemical Reviews, Ralph Shriner Editor, Vol. 46, 1950 pp. 406-470 Published for The American Chemical Society by The Williams & Wilkins Co. Baltimore, 1950, and in Rodd's Chemistry of Carbon Compounds, second edition, Edited by S. Coffey et al. Vol IV, Part C Heterocyclic Compounds Martin F. Ensell, Editor, Elsevier, 1986 pp. 185 et seq., where the use of certain isocyanates in the synthesis of hydantoins from α-amino acids, including aspartic acid has been disclosed. Functional hydantoins have been incorporated into linear, as well as crosslinked, polymers, as disclosed in U.S. Pat. No. 3,549,599. Lastly, the preparation of polyester aspartates from polyesters and amines has been disclosed in the paper Comparative Chemical Reactions Between α,β-Unsaturated Polyesters and Monomeric Maleic and Fumaric Esters, Sung Ki Lee in Am. Chem. Soc. Div. of Organic Coatings and Plastic Chemistry, Miami Beach, April 1967, 27(1).

The present invention provides for a facile synthesis of a thermoreversible system useful as coating having applicability in imaging technology, protective and transit coatings. The term "thermoreversible" as applied in the present context describes a polymeric network which upon heating breaks up to form hydantoin.

DETAILED DESCRIPTION OF THE INVENTION

In accordance with the present invention a conventional unsaturated polyester (herein UPE) is reacted with a monofunctional amine to yield a poly(ester aspartate). In a subsequent step, the poly(ester aspartate) is reacted with an isocyanate to produce a poly(ester urea). The resulting poly(ester urea) is then cyclized upon heating to form the hydantoin compound. A schematic representation of the inventive process is represented as follows:

In the first step of the process an unsaturated polyester is formed conventionally. Detailed description of the conventional reactions for the formation of UPE may be found in Encyclopedia of Polymer Science and Engineering, Vol. 12, John Wiley & Sons, Inc., N.Y. 1988, pp.256-290 and in Encyclopedia of Chemical technology, Vol 18, John Wiley & Sons, Inc. N.Y., (1978) pp. 575-594 and the references cited therein, the disclosures of all being incorporated herein by reference. The reaction is preferably carried out at 100°-220° C. for a time sufficient to attain the desired hydroxyl and acid numbers. The reaction time can be shortened by the use of transesterification catalysts, usually added at a concentration of about 500-5000 PPM. Examples of transesterification catalysts include: Tetrabutyl titanate, tetrabutyl zirconate, zirconium naphthenate, butyltinoxide hydroxide, dibutyltin diaceate, sodium acetate, sodium phosphate, zinc salts, strong Bronsted acids such as p-toluene sulphonic acid and sulphuric acid.

Shorter reaction times can also be achieved by the use of vacuum (down to about 0.5 mm Hg) during the latter part of the polymerization. The UPE's (unsaturated polyesters) are characterized in that their molecular weight is about 144-15000 g/mol, preferably 500 to 10,000 g/mol and most preferably 500 to 5,000 g/mol and in that their acid number is less than 10 mg KOH/g and that their OH number is about 0 to 300 mg KOH/g. Preferably the acid number is less than 5 mg KOH/g, and the OH number is about 10-100 mg KOH/g.

Depicted below is the reaction representative of the first step of the process: in the depiction, a diol, optionally a saturated diacid, and a unsaturated monomer containing the structural unit

such as maleic anhydride or maleic acid or fumaric acid are reacted to form an unsaturated polyester represented by IV. The optional diacid are used to lower the amount of unsaturation in the resulting polyester. Also optionally included in the synthesis for controlling the molecular weight and determining the end-groups are monofunctional acids and alcohols. Examples include propionic acid, benzoic acid, and saturated or unsaturated fatty acids such as stearic and oleic acids. In the representation below, $R_1$ and $R_2$ independently denote aliphatic, aromatic, cycloaliphatic or araliphatic radicals having 2 to 30, preferably 2 to 15, most preferably 2 to 8 carbon atoms. Examples of suitable diols include ethylene glycol, 1,2- and 1,3-propanediol, 2-methyl-1,3-propanediol, 2,2-dimethyl-1,3-propanediol, 1,2- and 1,4-butanediol, 1,4-bis-(hydroxymethyl)cyclohexane, 1,2- and 1,4-cyclohexanediol. Examples of the optional diacids include adipic-, glutaric- and succinic acids, phthalic-, isophthalic-, and terephthalic acids and phthalic anhydride. $R_1$ and $R_2$, independently one of the other, may optionally be substituted by any of halogen atoms, ether or thioether radicals.

In an additional embodiment of the invention, the polyester may be end-capped. End-capping may be attained during the polyester synthesis by using mono acids or mono alcohols as mentioned above. Alternatively, end-capping may be attained after the synthesis by reacting the polyester with a hydroxy or carboxylic acid reactive species. End-capping groups include tetrahydropyranyl, methyl-, ethyl-, silyl- and benzyl ethers, methyl-, ethyl-, silyl- and benzyl esters. Preferred groups include tetrahydropyranyl, benzyl ester and benzyl ether.

The ratio of the unsaturated monomers (such as maleic anhydride, maleic acid or fumaric acid) to saturated monomers determines the molecular weight of the hydantoin of the invention: the more unsaturated monomers the lower the molecular weight. In a preferred embodiment the molar ratio of III to the sum of I and II is about 0.14 to 1.

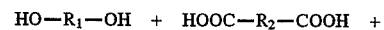

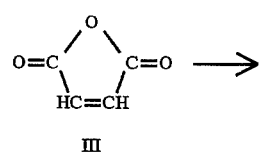

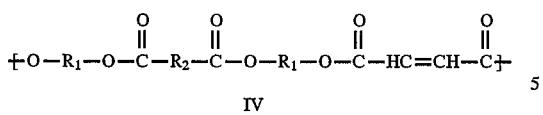

IV

In accordance with the inventive process the polyester, such as the one conforming to IV above is reacted with a monofunctional amine to form the corresponding poly(ester aspartate) —V below— in accordance with the schematic representation below:

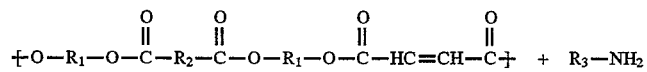 + $R_3-NH_2$

IV

↓

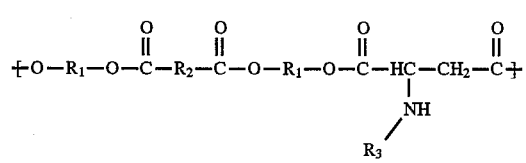

V wherein $R_3$ denotes aliphatic, aromatic, cycloaliphatic or araliphatic radicals having about 1 to 24, preferably 1 to 15, and most preferably 1 to 10 carbon atoms. These radicals may be substituted by halogen atoms, ether or thioether groups. Among the suitable amines mention may be made of cyclohexylamine, methylcyclohexylamine, methylamine, ethylamine, propylamine, decylamine, octadecylamine and oleylamine. The reaction conditions are known and have been reported in the paper Comparative Chemical Reactions Between α,β-Unsaturated Polyesters and Monomeric Maleic and Fumaric Esters, Sung Ki Lee in Am. Chem. Soc. Div. of Organic Coatings and Plastic Chemistry, Miami Beach, April 1967, 27(1), and in U.S. Pat. Nos. 5,126,170 and 5,243,012 the disclosures of which documents are incorporated herein by reference. The reaction is preferably carried out either neat or in a solvent such as toluene or xylene at 30°–100° C. in a molar ratio of amine to unsaturation repeat units of about 0.1:1 to 1:0.5; excess amine may be removed by distillation upon completion of the reaction.

The poly(ester aspartate) thus made is in accordance with the invention reacted with an isocyanate to produce a poly(ester urea) in accordance with the schematic below:

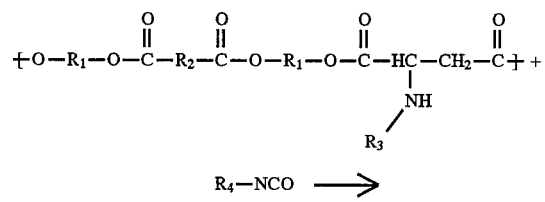 +

$R_4-NCO$ 

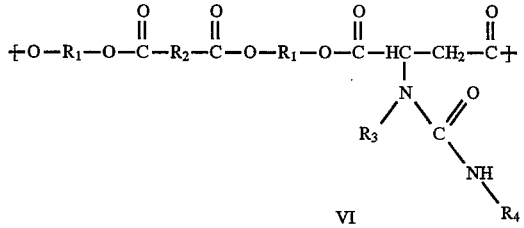

VI wherein $R_4$ denotes aliphatic, aromatic, cycloaliphatic or araliphatic radicals having about 1 to 50, preferably 4 to 25 carbon atoms. These radicals may be substituted such as by halogen atoms or isocyanate groups. The isocyanates suitable in the present context include organic compounds having one or more isocyanate groups per molecule. Suitable polyisocyanates are described, for example in U.S. Pat. Nos. 5,124,427; 5,208,334; 5,235,018; 4,065,410; 3,401,180; 3,454,606; 3,152,162; 3,492,330; 3,001,973; 3,594,164 and 3,164,605, all incorporated by reference herein. Included among the suitable aromatic polyisocyanates are 2,4- and 2,6-toluene diisocyanate, diphenylmethane diisocyanate, p-phenylene diisocyanate, polymethylenepolyphenylpolyisocyanate, and mixtures thereof and the like. Also useful are polymeric derivatives of diphenylmethanediisocyanate as well as prepolymers or quasi-prepolymers thereof. Also useful are the hydrogenated derivatives of the foregoing aromatic polyisocyanates as well as hexamethylene diisocyanate, isophorone diisocyanate, and the like.

Suitable monomeric diisocyanates may be represented by the formula $R(NCO)_2$ in which R represents an organic group obtained by removing the isocyanate groups from an organic diisocyanate having a molecular weight of about 112 to 1,000, preferably about 140 to 400. Diisocyanates preferred for the process according to the invention are those represented by the above formula in which R represents a divalent aliphatic hydrocarbon group having 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 2,2,4-trimethyl-1,6- hexamethylene diisocyanate, 1,12-dodecamethylene diisocyanate, cyclohexane-1,3- and -1,4-diisocyanate, 1-isocyanato-2-isocyanatomethyl cyclopentane, bis-(4-isocyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4(3)-isocyanatomethyl cyclohexane, 2,4- and/or 2,6-hexahydrotoluylene diisocyanate, 1,3- and/or 1,4-phenylene diisocyanate, 1,5-diisocyanato naphthalene and mixtures thereof. Aromatic poly-isocyanates containing 3 or more isocyanate groups such as 4,4',4"-triphenylmethane triisocyanate may also be used.

In accordance with the present invention the polyisocyanate component may also be in the form of a polyisocyanate adduct. Suitable polyisocyanate adducts are those containing isocyanurate, uretdione, biuret, urethane, allophanate, carbodiimide and/or oxadiazinetrione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, U.S. Pat. No. 4,288,586 and U.S. Pat. No. 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a trialkyl phosphine catalyst and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight and an (average) NCO functionality of 2 to 4.5.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Carbodiimide group-containing polyisocyanates which may be prepared by oligomerizing di- or polyisocyanates in the presence of known carbodiimidization catalysts as described in DE-PS 1,092,007, U.S. Pat. No. 3,152,162 and DE-OS 2,504,400, 2,537,685 and 2,552,350.

8) Polyisocyanates containing oxadiazinetrione groups and containing the reaction product of two moles of a diisocyanate and one mole of carbon dioxide.

In preparing the poly(ester urea) in the context of the present invention, the embodiments entailing aromatic isocyanates the reaction temperature is preferably at most 30° C., in corresponding reactions where the isocyanate is non-aromatic the reaction temperature is preferably at most 60° C. The reaction may be catalyzed by known acidic catalysts, including protic and Lewis acids, for instance octanoic acid and dibutyltin dilaurate.

The poly(ester urea) thus prepared is heated to produce hydantoin (VIII)

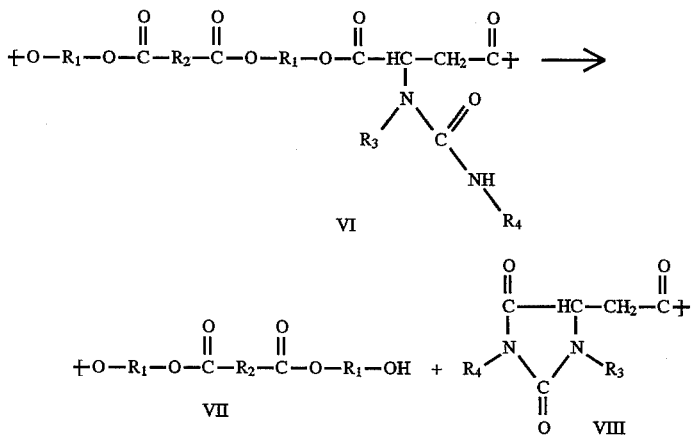

using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

In embodiments based on aromatic or substituted isocyanates, the reaction temperature is at least 30° C. and in the embodiments entailing non-aromatic isocyanates, the reaction temperature is at least 60° C. The reaction may be catalyzed by acidic or by basic catalysts. Preferred catalysts include acetic acid and tertiary amines, especially triethylenediamine.

The inventive process described above results in the formation of hydantoin. The formation is accompanied by a sharp reduction in the molecular weight and crosslink density of the polyester backbone, as well as a change in its solvent resistance and adhesive properties. The process of the invention, including the formation of hydantoin and the accompanying change in properties makes the process suitable in a number of applications including lithography. In applying the inventive process to lithography, a poly(ester urea) film is applied to a substrate. The image to be reproduced is transferred to the film by the use of a heat source. The changes in the solvent resistance and in the adhesion to the substrate of the heated areas make the process useful in lithography. Applications requiring a protective coating, where the coating protecting a substrate is removed by the application of heat, may also find the process disclosed in this invention useful.

EXAMPLES

1. The preparation of unsaturated polyester 124 g maleic anhydride, 555 g adipic acid, 286 g 2,2,-dimethyl-1,3-propanediol, 248 g 2-methyl-1,3-propanediol, and 0.40 g hydroquinone were mixed in a round bottom flask equipped with a Dean Stark trap, a thermocouple and an overhead stirrer, and heated under nitrogen atmosphere to 150° C. After 2 hours the temperature was increased to 170° C. and after an additional 2 hours to 190° C. where the reaction was kept for 3 hours. Then the pressure was successively lowered to about 5 mm Hg during a 7 hour period, and then kept at this pressure for 10 hours. The resulting unsaturated polyester had an acid number of 3.7 mg KOH/g and an hydroxyl number of 31.1 mg KOH/g, indicating a molecular weight of about 3200 g/mole.

2. The preparation of end-capped unsaturated polyester 26 g of benzoylchloride in 100 ml of methylene chloride was slowly added to a cold (0°–5° C.) solution of 220 g of an unsaturated polyester ($M_n$=2600 g/mole) and 19 g of triethylamine in 1000 ml of methylene chloride. After complete addition the temperature was increased and the reaction mixture was kept at reflux for 2 hours. The sample was concentrated to about 500 ml and then washed repeatedly with water, 1.0 M HCl, saturated sodium bicarbonate solution, water, and saturated sodium chloride solution respectively. The resulting organic solution was dried over magnesium sulphate, filtered and concentrated. The hydroxyl number of the resulting end-capped, unsaturated polyester had diminished from 40 to 6 mg KOH/g.

3. The preparation of a polyester aspartate 93.0 g of an unsaturated polyester with an average equivalent weight of 211 g/mole was heated under nitrogen atmosphere at 60° C. in a three-neck flask equipped with an overhead stirrer, a thermocouple and a condenser. 43.6 g of cyclohexylamine was slowly added at a rate that kept the temperature below 80° C. After complete addition the temperature was maintained at 80° C. for 6 hours, at which point the reaction was complete, e.g., measured by unsaturation titration.

4. The preparation of a poly(ester urea) coating 15.9 g of a poly(ester aspartate) with an average equivalent weight of 552 g/mole was mixed with 2.2 g of methylethyl ketone and 7.0 g of a polyfunctional aliphatic polyisocyanate resin based on hexamethylene diisocyanate to give a NCO/NH ratio of 1.1:1. The formulation had a dry-to-touch time of 1 min.

5. The preparation of a hydantoin in a poly(ester urea) coating

The formulation in Example 4 was applied to a cold-rolled steel plate using a doctor blade to give a wet-film thickness of 150 μm. Films were dried at 25°, 60° and 100° C. respectively, and the solvent resistance was monitored by methethyl ketone (MEK) double rubs (rubbing of a solvent-soaked cotton ball over the film surface until a marred or broken surface is produced). The room temperature cured film showed a very high solvent resistance and the film surface was intact after 200 double rubs. The films cured at 60° C. and 120° C. for 120 min. broke after 48 and 3 double rubs, respectively. This dramatic loss of solvent resistance clearly demonstrates the formation of hydantoin species accompanied by the reduction of polymer molecular weight.

What is claimed is:

1. A thermoreversible process for the preparation of a hydantoin comprising
   (a) reacting an unsaturated polyester with a monofunctional amine to yield a poly(ester aspartate), and
   (b) reacting said poly(ester aspartate) with an isocyanate to produce a poly(ester urea), and
   (c) heating said poly(ester urea) to form a hydantoin compound, wherein said unsaturated polyester is the product of a reaction of a compound containing a structural unit conforming to

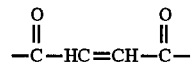

and at least one diol.

2. The process of claim 1 wherein said compound containing said structural unit is least one member selected from the group consisting of maleic anhydride, maleic acid and fumaric acid.

3. The process of claim 1 wherein said reaction further comprises a saturated diacid.

4. The process of claim 3 wherein the molar ratio between said compound containing said structural unit to the molar sum of said diol and said diacid is about 0.14 to 1.

5. The process of claim 1 wherein said monofunctional amine conforms to $R_3NH_2$ wherein $R_3$ denotes aliphatic, aromatic, cycloaliphatic or araliphatic radicals having about 1 to 24 carbon atoms.

6. A thermoreversible coating comprising poly(ester urea) prepared by
   (a) reacting an unsaturated polyester with a monofunctional amine to yield a poly(ester aspartate), and
   (b) reacting said poly(ester aspartate) with an isocyanate to produce a poly(ester urea), wherein said unsaturated polyester is the product of a reaction of a compound containing a structural unit conforming to

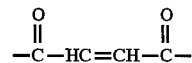

and at least one diol.

7. The coating of claim 6 wherein said compound containing said structural unit is least one member selected from the group consisting of maleic anhydride, maleic acid and fumaric acid.

8. The coating of claim 6 wherein said reaction further comprises a saturated diacid.

9. The coating of claim 8 wherein the molar ratio between said compound containing said structural unit to the molar sum of said diol and said diacid is about 0.14 to 1.

10. The coating of claim 6 wherein said monofunctional amine conforms to $R_3NH_2$ wherein $R_3$ denotes aliphatic, aromatic, cycloaliphatic or araliphatic radicals having about 1 to 24 carbon atoms.

* * * * *